United States Patent [19]

Motsenbocker

[11] Patent Number: 5,043,288

[45] Date of Patent: Aug. 27, 1991

[54] IMMOBILIZE MOLECULAR BINDING PARTNERS TO CONTACT ACTIVATING SUPPORTS

[76] Inventor: Marvin A. Motsenbocker, 11013 Anderson Lakes Pkwy. 313E, Eden Prairie, Minn. 55344

[21] Appl. No.: 208,984

[22] Filed: Jun. 20, 1988

[51] Int. Cl.$^5$ ............... G01N 33/543; G01N 33/537; C12P 21/06; A61K 35/14

[52] U.S. Cl. .................................. 436/518; 436/527; 436/538; 436/807; 436/821; 435/7.1; 435/7.92; 435/69.1; 530/380; 530/387; 530/389; 530/808; 530/810

[58] Field of Search ............... 436/518, 501, 527, 536, 436/538, 807, 808, 821; 530/380, 387, 389, 808, 810; 435/7, 70, 172.3, 69.1

[56] References Cited

U.S. PATENT DOCUMENTS

| | | | |
|---|---|---|---|
| 3,519,538 | 7/1970 | Messing et al. | 435/176 |
| 3,556,945 | 1/1971 | Messing | 435/176 |
| 3,652,761 | 3/1972 | Weetall | 436/527 |
| 3,983,000 | 9/1976 | Messing et al. | 435/176 |
| 4,363,634 | 12/1982 | Schall, Jr. | 436/527 |
| 4,657,873 | 4/1987 | Gadow et al. | 436/532 |
| 4,731,337 | 3/1988 | Luotola et al. | 436/526 |
| 4,777,145 | 10/1988 | Luotola et al. | 436/526 |

OTHER PUBLICATIONS

*Cecil Textbook of Medicine,* Wyngaarden et al., (ed.), "Disorders of Blood Coagulation", McKee, P. A., pp. 992–996, W. B. Saunders Company, Philadelphia (1983).
Scouten (ed.), *Solid Phase Biochemistry,* pp. 253–291.
Vroman et al., Blood, "Interact Ion of HMWK, Factor XII and Fibrinogen in Plasma at Interfaces", vol. 55, pp 156–159, 1980.
Brash & Samak, Journal of Colloid, "Dynamics of Interaction Between Human Albumin and Polyethylene Surface", vol. 65, No. 3 pp. 495–504, 1798.
Chuang et al. J. Lab. Clin. Med., "Interaction of Plasma Proteins with Artificial Surfaces: Protein Adsorption Isotherms", vol. 92, pp. 483–496, 1978.
Szycher, ed., Biocompatible Polymers, Metals and Composites, p. 82.
Griep et al., Biochem., "Possible Basis for the Apparent Surface Selectivity of the Contact Activation of Human Blood Coagulation Factor XII", vol. 25, No. 21, pp. 6688–6694, 1986.
Szycher, ed. Biocompatible Polymers, Metals and Composites, pp. 47–49.
McMullen and Fujikawa, J. Biol. Chem., "Amino Acid Sequence of the Heavy Chain of Human alpha Factor XIIa (Activated Hageman Factor)", vol. 260, p. 5328–5341, 1985.
Grinnell and Feld, J. Biomed. Mater. Res., "Adsorption Characteristics of Plasma Fibronectin in Relationship to Biological Activity", vol. 15, pp. 363–381, 1981.
Que and Davie, Biochem., "Characterization of a cDNA Coding for Human Factor XII (Hageman Factor)", vol. 25, pp. 1525–1528, 1986.
Cochrane and Griffin, Am. J. Med., "Molecular Assembly in the Contact Phase of the Hageman Factor System", vol. 67, pp. 657–64, 1979.
Weerasinghe, Biochem. Biophy., "A Rapid Method for the Isolation of Coagulation Factor XII from Human Plasma", vol. 839, pp. 57–61 1985.
Ford et al., Immunochem., "Characterization of Glutaraldehyde Coupled Alkaline Phosphatase Antibody and Lactoperoxidase Antibody Conjugates", vol. 15, pp. 237–243, 1978.
Reid et al., Am. J. Med. Technol., "Evaluation of Fluorescein Conjugated Antisera in the Clinical Laboratory", vol. 39, pp. 315–320, 1973.

*Primary Examiner*—Esther L. Kepplinger
*Assistant Examiner*—Janelle Graiter

[57] ABSTRACT

Molecular binding partners such as antibodies and haptens are immobilized to support materials that have the property of contact activation of blood protein coagulation. A binding partner is attached to a surface-active protein carrier and the resulting conjugate non-covalently adsorbs onto the surface of the support. The method provides for diagnostic assays of greater sensitivity and convenience.

15 Claims, No Drawings

IMMOBILIZE MOLECULAR BINDING PARTNERS TO CONTACT ACTIVATING SUPPORTS

BACKGROUND OF THE INVENTION

1. Field of the Invention

This invention relates generally to the field of immobilized proteins, and specifically with immunological binding partners which have been immobilized onto support materials. These support materials are primarily inorganic and have the property of contact activation of blood proteins.

2. Description of the Prior Art

The development of procedures to immobilize antibodies, other proteins and haptens onto a solid phase has provided extremely useful analytical methods for detecting and quantitating various organic substances of medical, environmental and industrial importance which appear in liquid mediums at very low concentrations. Diagnostic test kits which embody these procedures allow rapid and convenient tests to be performed. During use of a test kit a biological fluid that contains analyte at unknown concentration is usually combined with a solid phase support and with other chemical substances. The solid phase surfaces used in these diagnostic test kits frequently contain immobilized antigen (hapten) or, antibody that participates in competitive binding reactions or binding pair formation reactions. These binding reactions precede a signal development reaction in which the concentration of analyte to be detected is correlated to a change in a measurable quantity such as a light signal or electrical current.

Substances that participate in binding pair formation reactions are termed binding partners. Examples of such binding partners are avidin, biotin, antibody fragments, and haptens. The binding reactions are characterized by high affinity (strong association) between binding partners. The association constants for these reactions may be as high as $10^{10}$. The association between binding partners has to be controlled so that desorption of binding partner from the solid support is minimized. One aim of the art is to minimize this desorption.

Proteins and other types of binding partners have been immobilized or fixed on a wide variety of materials, both organic and inorganic. For example, antibodies and other proteins have been covalently immobilized to organic polymers by diazotization, amide bond formation, Schiff's base formation, Ugi reaction, amidination reactions and by crosslinking the protein in place with agents such as glutaraldehyde. Non-covalent techniques have also been used to couple substances to the surfaces of organic materials. For example, plastic surfaces may be coated with defined compositions of hydrophobic amino acids and then further treated with covalent coupling compounds as taught by Gadow and Wood in U.S. Pat. No. 4,657,873 issued (4/14/87) and entitled "Preactivated Plastics Surfaces for Immobilizing Organo-chemical and Biologic Materials". A brief summary of protein immobilization techniques may be found in Solid Phase Biochemistry, (1983) pp. 253-291 (ed. William H. Scouten).

Although most solid phase materials used in immunodiagnostics utilize antibody, antibody fragment, or hapten coupled to supports made of organic polymers, inorganic supports are sometimes preferable. Glass is especially desirable as a support medium because of its optical and mechanical properties and because it is chemically inert. Glass tubes in particular are desirable because of their relatively low cost and adaptability as cuvettes directly to colorimeters and nephelometers commonly available on the market. Glass fiber is used in some diagnostic procedures as a solid phase filter to immobilize red blood cells and other particles because of its mechanical rigidity and chemical inertness.

Unfortunately, the desirable chemical inertness of inorganic materials makes it difficult to immobilize molecular binding partners to them. Procedures used to covalently attach binding partners to inorganic materials require chemical modification of the surface to generate active residues that can in turn be chemically coupled to protein or other biologically active substances. For example, see U.S. Pat. No. 3,519,538 to Messing et al. issued (7/7/70) and entitled "Chemically Coupled Enzymes" disclosing enzymes bound via silanes and U.S. Pat. No. 3,652,761 to Weetall issued (3/28/72) and entitled "Immunochemical Composites and Antigen or Antibody Purification Therewith" disclosing antibodies bound via silanes. Messing and Odstrchel made a significant improvement to this early prior art by reacting siliceous support material with /-dianisidine and washing prior to contacting the activated support with protein solution (U.S. Pat. No. 3,983,000) issued (9/28/76) and entitled "Bonding Proteins to Inorganic Supports". Although an improvement, this procedure still requires multiple incubation and wash steps prior to contact of the inorganic support with a desired molecular binding partner. Coating of support material with a solution as taught by Schall, Jr. in U.S. Pat. No. 4,363,634 issued (10/18/83) and entitled "Glass Support Coated with Synthetic Polymer for Bioprocess" is applicable to glass supports but this procedure requires a separate coating step with polymeric film to form a surface layer on the glass and also a separate curing step of that film.

It cannot be overemphasized that the complexity of coating the solid support with molecular binding partners is a major determinant to the cost and manufacturing reproducibility (quality) of the diagnostic system. Ideally, one would like to simply contact a support with a solution that contains the binding partner to be adsorbed and then dry it. Passive adsorption of protein to glass prepared by acid washing was taught by Messing in U.S. Pat. No. 3,556,945 issued (1/19/71) and entitled "Enzyme Stabilization". In this passive adsorption procedure the glass surface is pretreated with acid, the passive adsorption step requires from 1 to 72 hours of incubation and the adsorption step is followed by a lengthy leaching step that may be a matter of hours and even up to many days. Furthermore, the desorption of protein from glass surfaces is a common and well recognized problem when prepared glass surfaces come into contact with blood proteins. For example, Vroman et al. reported the desorption of fibrinogin that had passively adsorbed onto "glass like" surfaces in Blood. 55, 156-159 (1980) and Brash and Samak discovered adsorbed serum albumin to become confromationally altered and slowly diffuse into solution from solid surfaces (J. Colloid Interface Sci. 65, 495-504 (1978). In some cases it was shown that although the total amount of protein adsorbed onto surfaces remains the same, there is exchange with soluble protein in solution which contacts the surface. For an example, see Chuang et al. J. Lab. Clin. Med. 92, 483-496 (1978). Thus, any solid support coated with passively adsorbed protein is at risk of protein desorption when the support is exposed to high levels of protein such as that found in blood or serum fractions. Trace amounts of certain proteins in blood irreversibly bind to "contact activation" surfaces and can even displace or cause removal of protein previously adsorbed onto these surfaces (Biocompatible Polymers, Metals, and Composites (1983) p. 82).

Although poorly understood, the interaction of chemical substances with solid surfaces is important to the performance of diagnostic tests. Most fluids that contact surfaces used in these assay kits contain proteins. These proteins bind to and cover up sites on the vessal walls and on the solid phase support materials used for separation. Supports having different compositions are susceptible to this phenomenon in different ways. Complement activating supports are materials that activate the blood complement cascade system of plasma. Many materials having this property have been studied. Examples are glass, diamataceous earth, kaolin, crystals, soluble polymers such as dextran sulfate, crude preparations of collagen, microparticles and micelles such as sulfatides. The common features of these materials are negative charge and a high molecular mass (Griep et al. Biochem. 25, 21, 6688–6694 1986). The blood complement cascade system of plasma is comprised of proteins that interact with complement activating surfaces and/or each other. One result of the contact of complement activating support with plasma protein is clot formation.

Most medical diagnostic procedures require contact of the solid phase with blood or serum fractions. The solid supports used in such procedures are thus unusually susceptible to protein adsorption/desorption phenomena discussed above. Because of this blood component induced desorption problem associated with use of coated glass surfaces prepared by passive adsorption, tedious covalent coupling techniques have heretofore been used to adsorb molecular binding partners to glass. Any method that both overcomes the need for covalent coupling and eliminates or substantially reduces adsorption/desorption interference is therefore an important enhancement to the art.

The present invention provides certain proteins having exceptional affinities for contact activating surfaces (surface active) that can be used to link other proteins or binding substances to supports having these surfaces such that they remain bound to such supports in the presence of blood or serum. These surface active proteins are immune to desorption from complement activating supports in the presence of blood or blood fractions because they substantially resemble blood protein that participates in the blood complement activation system and are not displaced by these same proteins. Descriptions of these proteins and details of using them are disclosed herein.

SUMMARY OF THE INVENTION

The general purpose of the present invention is to prepare composites of immobilized biologically active proteins for diagnostic purposes. The method is allowed by use of special "surface active" protein linkers capable of non-reversibly binding to solid supports. The method comprises coupling "surface active" protein to desired biologically active compounds or protein, and then contacting a water solution of the prepared couple protein complex with the water insoluble support material having binding sites for the surface active protein. In the preferred embodiments, the prepared coupled protein complex comprises significant peptide sequence homology with the binding region (NH3 terminal sequence) of blood protein factor XII or comprises significant homology with the surface binding site region of activated high molecular weight kininogen and said complex non-covalently binds to a complement activating support having a polyanionic surface.

Another purpose of the present invention is to utilize the properties of blood protein interactions with complement activating supports to improve convenience of binding member immobilization to support materials used in diagnostics. Still another purpose is to prevent removal of trace amounts of adsorbed protein from support material by using carrier protein that resembles the displacing protein and which binds essentially irreversibly. Still another purpose is to improve kinetics of binding within the diagnostic procedure itself. This is achieved by allowing immobilization of a binding pair member after or during fast binding pair formation reaction in solution rather than slow binding pair formation on a solid phase. Yet another purpose of the invention is to provide excess carrier protein to lower the background signal development in certain heterogeneous immunoassays that utilize a signal generating protein conjugate reagent.

Surface active proteins in the context of the present invention are polypeptides that substantially resemble the binding portions of these proteins that have high affinity for complement activating supports.

The following proteins meet the criteria of surface active proteins and are included in this group: factor XII (hageman factor), HMWK (high molecular weight kininogen), fibrinogen and fibronectin. Complement activating supports are various negatively charged surfaces having the common features of highly dense negative charge and a high molecular mass (more than 100,000 daltons) Glass, fibrin, collagen, kaolin, dextran sulfate and sulfatide are most common examples of complement activating supports. Glass is a common complement activating support having a polyanionic surface, but other silicaceous surfaces lacking a surface charge (e.g., silicone treated surface) are not complement activating. Thus, having a negative surface charge is an important attribute of these supports. Many blood proteins adhere to complement activating supports and can be found in trace quantities there.

For example, adsorption of serum albumin and IgG to surfaces has been extensively studied (Biocompatible Polymers, Metals, and Composites pp. 47–49 (1983) ed. M. Szycher). Although these proteins account for the majority of plasma protein they adsorb much more poorly to complement activating surfaces than do HMWK (high molecular weight kininogen) or factor XII (hageman factor). HMWK and factor XII are present in plasma in trace amounts yet these proteins can be found on the surfaces of complement activating supports at least 100 fold more concentrated than the more abundant proteins serum albumin and antibody (IgG). Thus, a distinguishing feature of these surface proteins is that they have high affinity for complement activating supports and can be considered to irreversibly bind to these supports. Fibrinogen is a surface active protein in the absence of HMWK and factor XII or with complement activating supports having texture or geometry creating narrow spaces or where flow is reduced since it is preferentially adsorbed over other plasma protein under these conditions. A particularly useful application for fibrinogen as a carrier would be for assay of analytes present in aqueous fluids that lack factor XII and HMWK (eg. urine, saliva, water supplies). Fibronectin can similarly be considered a surface active protein with contact activating supports since it mediates adhesion of fibroblasts to glass, fibrin, and certain physical forms of collagen. Fibronectin is also included in this group of proteins because it is incorporated into clots formed after wounding and promotes thrombus formation under some conditions (Grinnell and Feld J. Biomed. Mater. Res. 15, 363-381 (1981).

One advantage of the present invention is a decrease in unwanted background signal during use of the diagnostic system. The detection limit of the assay system is frequently limited by this background signal and anything which minimizes the background signal will often improve assay performance. Many diagnostic systems utilize a protein conjugate to generate a readily detectable signal and modulation of that signal occurs by modulating the binding of protein conjugate to the support. The signal generating protein conjugate is usually at a high concentration and some of it non-specifically binds to the support. This non-specifically bound protein conjugate creates the unwanted background signal. Blood protein factor XII and HMWK are preferred as additives to limit background signal because they have unusually high affinities for complement activating supports and also because these two proteins have the further desired property of displacement of other adsorbed protein from the support. These two phenomena allow surface active protein to prevent non-specific binding of signal producing conjugate protein. The surface active protein preferentially binds the support, covers up the non-specific binding sites and facilitates removal of non-specifically bound conjugate from the support surface. The surface active protein used in this context may be conjugated with a second protein to more efficiently cover up the non-specific binding sites used by the signal producing conjugate.

An additional advantage of using surface active protein as an additive is that it will prevent adsorption of other protein onto solid surfaces. Currently, most diagnostic test kit solutions contain added filler, protein such as bovine serum albumin or casein at high concentrations to prevent small amounts of diagnostic assay ingredients from adsorbing to vessal walls and thus being removed from solution. Surface active proteins are more efficient at binding to and covering up binding sites on the solid surface and can thus be added at much lower concentrations to replace the added filler protein. This is particularly desirable when the protein content of a diagnostic test composition needs to be minimized.

Until now, protein factorpXII and HMWK have been expensive to prepare in large quantities because they are normally present at low concentrations in mammalian blood plasma. The portion of protein XII that binds to complement activating supports has been shown to be within the forty kilodalton amino terminal end of the protein (McMullen and Fujikawa J. Biol. Chem. 260, 5328-5341 (1985). The entire polypeptide of protein factor XII or a smaller polypeptide can be synthesized either in vitro or by molecular cloning techniques and harvested from micro-organism cell culture or from eukaryotic cell culture. Recently, a DNA sequence that codes for factor XII protein has been cloned and characterized (Que and Davie Biochem. 25, 1525-1528 (1986)). Expression of cloned DNA from micro-organism or eukaryotic cell culture would result in production of large quantities of low cost polypeptide having the ability to bind complement activating supports. In a similar manner, the histidine-rich cluster region of the HMWK polypeptide responsible for binding to contact activation supports (Lochrane and Griffin Am. J. Med. 67, 657-664 (1979)) or the entire polypeptide can be made available more cheaply by cloning technology.

DESCRIPTION OF THE PREFERRED EMBODIMENTS

Attachment of a binding partner to carrier protein can be done by any of a number of methods described in the prior art. Most common are covalent techniques that utilize a crosslinking agent such as water soluble forms of carbodiimide or glutaraldehyde. If the carrier protein is to be prepared by expression of modified or cloned DNA then the binding partner may be a stretch of polypeptide contiguous with the carrier protein and both members may be profitably synthesized as one protein for maximum economy of use. In this case, the sequence of poly-nucleic acid to be cloned contains both carrier polypeptide sequence information and binding member polypeptide sequence information. A single polypeptide or protein is then expressed having structural features of both carrier protein (binding site affinity for support) and binding pair member (binding site affinity for other binding pair member). A useful example is a protein that includes a factor XII portion and a human chorionic gonadotropin (hCG) portion. By placing both structural features in the same protein the hCG antigen can be more easily immobilized to complement activating surfaces, and also be more readily accessible for interactions in the solute phase. The later advantage accrues from placing a controlled sequence of polypeptide between the support binding site and the binding member. By having the binding member spaced further away from the support in this manner it is more available to interact with other solutes. Thus, kinetics for binding pair interaction are enhanced.

Non-covalent binding can be used to couple binding members or member conjugates to the carrier protein. The light chain of HMWK for example has binding sites for prekallikrein and factor XI. Prekallikrein, factor XI, or antibody directed against HMWK can be coupled non-covalently to HMWK. Such non-covalent coupling involves incubation of carrier with its coupling partner in aqueous solution either prior to use or during the diagnostic procedure. An advantage of using non-covalent coupling is that attachment of binding member to carrier may be carried out during the diagnostic procedure itself. This allows the binding member to interact with its binding partner in solution before becoming immobilized to the support. Because binding between binding members occurs in solution rather than at a solid support surface, kinetics are enhanced and the time duration of the diagnostic procedure can be considerably shortened.

Attachment of binding partner-carrier protein conjugate to the above mentioned support may be carried out in one step using conjugate at a concentration which is lower than that needed to saturate binding sites on the support or (if desired) at a higher concentration and followed by a wash step. Attachment occurs by contacting the support with a buffered aqueous solution of conjugate and allowing the conjugate time to adsorb to the support. The treated support may be dried for convenience.

In some cases, it is preferred to allow both binding pair members to remain free in solution prior to immobilization of one member to the support. In such cases, one binding member is coupled to surface active carrier protein and the coupled complex is not immobilized to the support until the binding pair reactions are substantially completed. This is most conveniently carried out by incubating binding pair members in solution prior to or at the same time as contact of said solution with support material. In this case the support material need not be processed during manufacture of the test kit because the immobilization reaction is performed during the diagnostic assay. Another advantage of this technique is simplification of the diagnostic procedure because the support does not have to contact the analyte solution or any binding member except that which is conjugated to carrier protein. Thus, the support may be combined with other diagnostic assay components during sample fluid addition, after binding reactions have started, or immediately prior to a wash step.

MODE OF OPERATION

The following is offered by way of illustration and not by way of limitation.

EXAMPLES

All temperatures are in degrees centrigrade. All parts and percents are (unless indicated otherwise) by weight except for mixtures of liquids which are by volume. All solutions are aqueous. The following abbreviations are used:

h-hour; L-liter; RT-room temperature; min-minute; BSA-bovine serum albumin; PBS-50 mM sodium phosphate, 0.8% NaCl, 0.2% NaN3 pH 6.5; D.I. H2O-distilled water; factor XII-blood protein factor twelve; factor XIIa-activated blood protein factor twelve; wash solution-PBS with 0.1% BSA, 0.1% tween 20 added; substrate solution-10 mM p-nitrophenyl phosphate, 1M diethanolamine, 0.5 mM MgCl2 pH 9.8.

EXAMPLE 1

Coating of glass surface with antibody-Factor XII conjugate.

In this embodiment of the invention a support is coated with carrier protein that has antibody attached to it. The carrier protein-antibody conjugate desorbs significantly less in the presence of serum than does unconjugated antibody protein.

All steps described in this example utilize plastic or siliconized containers that are rinsed with polybrene (2 mg/ml) and distilled water immediately prior to use. Soybean trypsin inhibitor and NaN3 are added to all buffers to final concentrations of 22 mg/L and 0.2 gm/L respectively. Polybrene is added to all buffers at 50 mg/L except those used in coating solutions. Factor XII is purified by affinity chromatography as described by Weerasinghe et al (Biochim. Biophy. Acta (1985) 839, 57-61). A brief description is given here. In the procedure, soybean trypsin inhibitor and polybrene are added to 2.25 L of plasma (0.1 mg/ml and 0.36 mg/ml respectively). The solution is then brought to 25% (NH4)2SO4 saturation. The precipitate is removed and the supernatant brought to 50% (NH4)2SO4 saturation. The second (25–50%) precipitate is dissolved in 2.25 L of saline and dialyzed against PBS. Zinc chelate-Sepharose is prepared from oxirane activated Sepharose 4B-CL and used for both of the following affinity chromatography steps. 300 ml of zinc chelate-Sepharose equilibrated with PBS are added to 2.25 L of the 25–50% dissolved precipitate fraction. After stirring slowly for 1 h at RT the mixture is poured into a siliconized Buchner funnel and washed with 29 L of PBS and 12 L of 0.02M sodium cacodylate/0.15M NaCl (pH 5.5). Factor XII protein from this first affinity chromatography step is eluted with 2.1 L of 0.1M sodium acetate/0.8M NaCl (pH 4.5). The eluted factor XII protein is then dialysed against 25 mM Na2HPO4, 5 mM sodium acetate, 0.8M NaCl (pH 6.5). For the second affinity chromatography step 320 ml of dialysed material are loaded onto a 50 ml column of zinc chelate-Sepharose equilibrated with the same buffer at 4 C. The column is developed with a pH gradient from pH 6.5 to pH 4.0 using 3 column volumes of the same buffer. To detect and measure Factor XII the column fractions are diluted, added to factor XII deficient plasma (Sigma, cat #B12D) and tested for clot formation time. Protein is measured with a Bradford dye binding assay (Sigma, cat #BCA-1). After purification, factor XII is concentrated to 4 mg/ml in PBS buffer.

The covalent coupling of antibody to Factor XII is carried out by the well recognized technique of glutaraldehyde crosslinking (for e.g. Ford et al Immunochem. 15, 237-243). Antibody protein specific for the alpha chain of hCG (human chorionic gonadotropin) is used (Sigma cat #C7409). Fluorescein label is conjugated to a portion of the antibody to allow fluorimetric measurement of low concentrations of the antibody. This is done by labelling 1% of the IgG with fluorescein via the method used by Reid et al (Am. J. Med. Technol. 39, 315-320 1975). Four mg of antibody are dissolved per ml of factor XII solution prepared above to give an approximate molar ratio of 2 factor XII molecules per antibody molecule. Since each specific antibody clone or antiserum preparation is different and has different reactivities with glutaraldehyde, the optimum ratio of antibody to factor XII may be profitably varied as much as 10 fold from this ratio to optimize yield. In addition, the concentration of glutaraldehyde used and/or the reaction time of protein with glutaraldehyde can be profitably optimized. Optimization of this reaction is described by Ford et al (Immunochem. 15, 237-243) and that method is utilized here. To optimize yield the following preliminary work is performed: A 25% stock solution of glutaraldehyde is diluted 250 fold into the two to one mixture of factor XII protein and antibody described above. This is incubated at RT and 50 ul portions are removed and added to 50 ul portions of 1 mg/ml sodium metabisulfite after 0 min, 10 min, 20 min, 40 min, 60 min, 120 min and 240 min. The degree of crosslinking at each time point is examined by polyacrylamide gel electrophoresis under non-denaturing conditions with 7% polyacrylamide. The reaction conditions (as revealed by gel electrophoresis band patterns) that yield crosslinked heterodimers of antibody and factor XII but that also minimize precipitation of protein are chosen as being optimum for conjugation. Conjugation under optimum conditions is then carried out using 4 mg of factor XII. After conjugation, the factor XII antibody conjugate material is purified by gel filtration chromatography over a plastic 1.5 cm by 75 cm column of Sephacryl S-300 equilibrated with PBS. Plastic test tubes are used to collect the column eluate. The aggregated protein fractions from the column eluate (that elute at the column void volume) are pooled and the ratio of antibody to factor XII determined by fluorescence and protein measurements. The fractions that contain at least one factor XII protein per antibody molecule are pooled into a plastic container and concentrated to 0.5 mg of antibody protein per ml solution. BSA is added to 10 mg/ml. For a control, the 1% fluorescein labelled antibody is diluted to 0.5 mg per ml of PBS solution and BSA is added to 10 mg/ml. The experimental and control protein solutions are stored at 4 degrees.

The solid phase to be coated consists of clean, new 12 mm diameter glass test tubes from American Scientific Products (cat #T1290-3). The glass tube coating procedure is: a one ml portion of protein solution (0.5 mg antibody per ml) is placed into a glass test tube and incubated at RT. After fifteen min the solution is removed and the tube briefly rinsed with 3 ml of wash solution. The fluorescence of the used coating solution is measured to determine how much coating solution IgG became bound to the tube. The solution is re-used to coat other (up to 4 more) glass tubes.

Five tubes are coated with factor XII-antibody conjugate and are designated "experimental" tubes. Five tubes are coated with antibody and are designated "control" tubes. One ml portions of undiluted serum are added to each tube. After one hour the tubes are decanted and rinsed twice with 3 ml of wash solution. The amount of IgG that desorbs from each tube into the decant and rinse solutions is determined by difference measurements using fluorometric analysis and by comparison to a standard curve of fluorescein labelled IgG. The tubes that are coated with antibody are found to desorb more than twice as much antibody (measured as fluorescence) than the tubes that are coated with factor XII-antibody conjugate.

EXAMPLE 2

Use of factor XII-antibody conjugate coated glass in an immunoassay format

In this embodiment the prepared tubes from example one are used to quantitate hCG (pregnancy hormone). The tubes coated with factor-XII antibody conjugate are found to perform better than tubes coated with antibody alone.

Glass tubes are coated with factor XII-antibody conjugate as described in example one. Another set of tubes are likewise coated with antibody (Bioproducts for Science Inc. Indianapolis, In. cat. N AHP205) by the same method described in example one. hCG male serum calibrator samples are purchased from Diagnostic Products Corp. (L.A., Ca., cat. KCGD1). One ml serum calibrator samples that contain 0, 1, 2, 5, 10, 20, 50, 100 and 200 mIU/ml hCG are mixed with a final concentration of 20 ug/ml antibody enzyme conjugate specific to the beta chain of hCG (Bioproducts for Science Inc. special order alkaline phosphatase hCG conjugate made from N AHP205). These solutions are added to each factor XII-antibody conjugate coated tube and to each antibody coated tube. The tubes are incubated for 60 minutes, decanted and briefly rinsed thrice with 3 ml of wash solution. One ml of substrate solution is then added to each tube and the tubes incubated at 35° C. for 15 min. After exactly 15 min each tube is briefly agitated and the absorbance of its contents measured at 410 nm on a spectrophotometer (readout step).

It will be seen that as the hCG concentration in the first incubation step is increased, a greater absorbance will be measured at the readout step. Also, the sample tubes that are coated with factor XII-antibody conjugate have a greater absorbance at the readout step than do the tubes coated with antibody alone. In addition, a lower concentration of hCG analyte is detected from the factor XII-antibody conjugate coated tubes than is detected from the tubes coated with antibody alone.

EXAMPLE 3

Contact Support Material with Liquid Coating Solution after Binding Reactions have been Substantially Completed In this embodiment adsorption of factor XII-antibody conjugate to a fibrous glass support occurs after binding of signal producing conjugate to sample analyte and binding of sample analyte to factor XII-antibody conjugate. A 10 cm by 5 cm sheet of whatman GFA glass fiber (Whatman, Ltd., Maidstone, England) is cut into 0.5 cm×1.0 cm elongate pieces and mounted onto one end of 0.5 cm ×10 cm elongate strips (0.04 cm thick) of polystyrene (Trycite@, Dow Chemical Co., Midland, Mi.) with double-faced adhesive tape (Part No. 2976MR, 3M Company, St. Paul, Mn). One half ml of incubation solution that contains 0.2% BSA, 10 ug factor XII-antibody conjugate and 10 ug antibody enzyme conjugate (Bioproducts for Science special order alkaline phosphatase hCG conjugate made from N AHP205) in PBS are separately pipetted into 9 plastic test tubes (American Scientific Products cat. T1225-22). One half ml of calibrator solutions (Diagnostic Products Corp. cat RKCG1) at 0, 5, 10, 20, 50, 100, 200, 500, and at 1000 mIU/ml concentration are separately added to the tubes and the resulting mixtures incubated for 30 min at room temperature. Then, a strip that contains laminated glass fiber is placed into each test tube and left for 5 min. After removal, each stick is rinsed 5 times in 2 ml of wash fluid. Each strip is then immersed into 2 ml of substrate solution at 35 C. After 15 minutes each tube is briefly agitated, the strip removed and absorbance of the tube contents determined at 410 nm. The development of color within the tubes during the readout step is found to be proportional to the concentration of hCG in the calibrator solution that was added to each tube.

EXAMPLE 4

Inhibition of Non-Specific Binding of Signal Producing Conjugate by Surface Active Protein In this embodiment factor XII is included in an incubation solution of signal producing conjugate with a siliceous surface in an immunoassay. Inclusion of this protein leads to lower non-specific binding of signal producing conjugate to the siliceous support.

Eighteen glass tubes are coated with antibody specific to the alpha chain of hCG as described in example two. hCG male serum calibrator samples are purchased from Diagnostic Products Corporation (cat. KCGD1). Antibody enzyme conjugate specific to the beta chain of hCG (Bioproducts for Science special order alkaline phosphatase hCG-b conjugate made from N AHP205) is added to 30 μg/ml to each serum calibrator including the zero level calibrator used for dilution. Serum calibrator samples are diluted to 0, 1, 2, 5, 10, 20, 50, 100 and 200 mIU/ml hCG. One half ml of each calibrator sample is added to each of two coated tubes. Fifty μg of factor XII protein is added to one tube of each calibrator concentration. All tubes are incubated for 60 minutes, decanted and briefly rinsed thrice with wash solution. One ml of substrate solution is then added to each tube and the tubes incubated at 35° C. for 15 min. After exactly 15 min the fluid in each tube is briefly agitated and the absorbance read at 410 nm on a spectrophotometer (readout step). It is seen that tubes that contain added factor XII protein have the lowest amount of non-specifically bound antibody enzyme conjugate (least amount of color development in the absence of hCG).

It will be understood that various modifications, changes, alterations and additions can be made in the method of the present invention, its steps and parameters. All such modifications, changes, alterations and additions as are within the scope of the appended claims form part of the present invention.

What is claimed is:

1. A method of preparing an immobilized binding member-support composition by absorbing a binding member carrier conjugate to a support material, said method comprising the steps of;
   a. forming a binding member carrier conjugate from a surface active carrier protein selected from the group consisting of factor XII, high molecular weight Kininogen (HMWK), fibrinogen and fibronectin and a binding member selected from the group consisting of antibody, antigen, hapten, avidin and biotin; and,
   b. contacting a complement activating support material having a high molecular mass and containing multiple negative charges with a solution of dissolved binding member carrier conjugate in an amount sufficient to coat said complement activating support material.

2. The method of claim 1, wherein said carrier protein is prepared by expression of recombinant DNA from cell culture.

3. The method of claim 1, wherein said carrier protein and said binding member are contiguous and are prepared by expression of recombinant DNA from cell culture.

4. The method of claim 1 wherein said complement activating support material is glass.

5. The method of claim 4 wherein said complement activating support material is in a fibrous form.

6. The method of claim 1 wherein after contact of said complement activating support material with said binding member carrier conjugate, said complement activating support material is washed and dried.

7. A method of measuring an analyte concentration by a sandwich assay method, the method comprising the steps of:
   a. simultaneously incubating a sample containing analyte with a binding member carrier conjugate comprised of binding member specific for the analyte conjugated to carrier protein selected from the group consisting of factor XII, HMWK, fibrinogen and fibronectin, and a second conjugate comprised of a second binding member specific for the analyte conjugated to a signal producing species, resulting in a complex of binding member carrier conjugate-analyte-binding member signal producing species conjugate;
   b. contacting a complement activating support material having a high molecular mass and multiple negative charges with the complex of step a resulting in the absorption of the complex to the support;
   c. separating the complement activating support material having the complex of step a absorbed thereto from unabsorbed conjugates; and,
   d. detecting a signal from the signal producing species in proportion to the amount of binding member carrier conjugate-analyte-binding member signal producing species conjugate complexes formed.

8. The method of claim 7, wherein said carrier protein is prepared by expression of recombinant DNA from cell culture.

9. The method of claim 7, wherein said carrier protein and said binding member are contiguous are prepared by expression of recombinant DNA from cell culture.

10. The method of claim 7 wherein said complement activating support material is glass.

11. The method of claim 10 wherein said complement activating support material is in a fibrous form.

12. In an ELISA assay method, including incubation of analyte with binding member immobilized to complement activating support material and with a second binding member conjugated to a signal producing species, and detection of a signal that is proportional to the amount of analyte, wherein the improvement comprises:
   inhibiting non-specific binding of binding member signal producing species conjugate to complement activating support material by incubating surface active protein selected from the group consisting of factor XII, HMWK, fibrinogen and fibronectin with complement activating support material in solution in an excess amount needed to bind all the available surface of the complement activating support material.

13. The method of claim 12 wherein said surface active protein is prepared by expression of recombinant DNA from cell culture.

14. The method of claim 12 wherein said complement activating support material is of high molecular weight and contains multiple negative surface charges.

15. The method of claim 12 wherein said complement activating support material is in a fibrous form.

* * * * *